United States Patent [19]
Becker et al.

[11] Patent Number: 5,068,317
[45] Date of Patent: Nov. 26, 1991

[54] DERIVATIVE OF HUMAN GROWTH HORMONE

[75] Inventors: Gerald W. Becker; Ralph M. Riggin, both of Indianapolis, Ind.

[73] Assignee: Eli Lilly and Company, Indianapolis, Ind.

[21] Appl. No.: 168,208

[22] Filed: Mar. 15, 1988

[51] Int. Cl.$^5$ ...................... A61K 37/36; C07K 13/00; C07K 15/00; C07K 17/00
[52] U.S. Cl. .................................... 530/399; 530/324; 530/350
[58] Field of Search ........................ 530/324, 399, 350

[56] References Cited
PUBLICATIONS

Houghten et al., *Archives of Biochemistry and Biophysics* 178, 350-355 (1977).
Teh et al., *J. Biol. Chem.*, 262, 6472-6477 (1987).
Riggin et al., *Analytical Biochemistry*, 167, 199-209 (1987).

*Primary Examiner*—Ronald W. Griffin
*Attorney, Agent, or Firm*—Joseph A. Jones; Leroy Whitaker; William C. Martens

[57] ABSTRACT

A sulfoxide of human growth hormone has been produced and characterized. The sulfoxide derivative arises from a selective oxidation of Met$^{14}$. The sulfoxide exhibits full biological activity.

1 Claim, No Drawings

DERIVATIVE OF HUMAN GROWTH HORMONE

BACKGROUND OF THE INVENTION

Large polyfunctional molecules such as proteins have the potential for forming a variety of derivatives of the original product. Indeed, modifications such as glycosylations and γ-carboxylations are well known and have been shown to have important physiological roles. Other modifications arise from the purification process. Degradation products also arise during storage of the protein. It is impossible a priori to know whether these structures will or will not have biological activity in their own right or the level and kind, if any, of such activity. Derivatives of pituitary derived human growth hormone (hGH) have been reported in the literature. Different size isomers of hGH have been detected in the plasma of both normal and acromegalic individuals. The predominant size isomer, the 22,000 dalton monomer, has been detected in several derivatized forms, including three proteolytically modified forms [Chramback, A., Yadley, R. A., Ben-David, M., and Rodbard, D. (1973) *Endocrinology* 93, 848-857; Singh, R. N. P., Seavey, B. K., Rice, V. P., Lindsey, T. T., and Lewis, U. J. (1974) *Endocrinology* 94, 883-891], an acetylated form and two deamidated forms [Lewis, U. J., Singh, R. N. P., Bonewald, L. F., Lewis, L. J., and Vanderlaan, W. P. (1979) *Endocrinology* 104, 1256-1265; Lewis, U. J., Singh, R. N. P., Bonewald, L. F., and Seavey, B. K. (1981) *J. Biol. Chem.* 256, 11645-11650]. Other hGH derivatives have been detected but have not been characterized. The recent use of recombinant DNA techniques to mass produce proteins of pharmaceutical interest has made it possible to attempt to prepare specifically modified products of the native recombinantly produced materials.

The availability of human growth hormone enabled us to discover and develop a method for producing a novel monosulfoxide derivative of human growth hormone, and it is to such derivative that this invention is directed. The compound of this invention is the sulfoxide of human growth hormone in which, of the three available methionine residues, the residue at position 14 is alone oxidized to its corresponding sulfoxide. For convenience, the compound of this invention is designated Met(O)$^{14}$-human growth hormone, or Met(O)$^{14}$-hGH. The compound of this invention unexpectedly exhibits a potency approximately equivalent to that of hGH itself.

DETAILED DESCRIPTION OF THE INVENTION

As noted, this invention is directed to Met(O)$^{14}$-hGH Houghten et al., *Archives of Biochemistry and Biophysics* 178, 350-355 (1977) reports studies of methionine oxidized human growth hormone in which two of the three and all three methionine residues were oxidized to sulfoxides. In the former, the methionine residues at positions 14 and 125 were oxidized. The product was found to exhibit about 25% of the potency of the native hormone. When all three residues (14, 125, and 170) were oxidized, major changes in all physical parameters measured were noted along with significant loss in growth-promoting activity.

Recently, Teh et al., *J. Biol. Chem.* 262, 6472-6477 (1987), reported studies on the sulfoxidation of hGH. Their data show (Table 1 and FIG. 1) that, applying their methodology, the order of sulfoxidation is such that the Met$^{125}$ is substantially more rapidly oxidized than the Met$^{14}$. The product(s) reported are logically, if any mono-sulfoxidation, the Met(O)$^{125}$-hGH, and the disulfoxidized Met(O)$^{14}$, Met(O)$^{125}$-hGH. Thus, the findings of Teh et al. would virtually preclude detectable formation of the compound of this invention.

The compound of this invention in all measured respects is equipotent to the native hormone.

Met(O)$^{14}$-hGH can be prepared from the native hormone by treatment with hydrogen peroxide as described in the following:

Two grams of biosynthetic human growth hormone (hGH) were dissolved in 200 ml of water and the pH was adjusted to 7.5 with concentrated ammonium hydroxide. Four millilters of 3% hydrogen peroxide were added and the solution was maintained at room temperature for four hours. One gram of methionine was added to the solution to quench the reaction. The protein solution was passed over a column packed with Sephadex G-25. The column was equilibrated in and the protein wa eluted using ammonia buffered water (pH 7.5). The resulting protein fraction was lyophilized and subsequently further purified by preparative reversed-phase HPLC using a column packed with Vydac, C$_{18}$ 300 Å pore diameter silica and measuring 22.5 x 250 mm. The oxidized hGH was dissolved in 50% tris buffer (50 mM tris HCl pH 7.5); 25& acetonitrile, 25% n-propanol at a concentration of 6.7 mg/ml and 400 mg were loaded onto the column. The protein was eluted from the column with a gradient generated from two solvents, A: 30% acetonitrile, 70% tris buffer (50 mM tris HCl pH 7.5) and B: 40% n-propanol, 60% tris buffer (50 mM tris HCl pH 7.5). The gradient was 66% B to 72% B over 150 minutes. The temperature of the column was maintained at 45° C. and the flow rate was 6 ml/min. Prior to loading the sample, the column was equilibrated with 66% B. Three columns were run as described and the fractions containing the hGH derivatives were pooled, passed over a column packed with Sephadex G-25 to remove the organic solvents and buffer salts, and lyophilized. As above, the G-25 column was equilibrated and the protein eluted using ammonia-buffered water (pH 7.5).

The highly purified product was shown to be the monosulfoxide derivative of hGH with the methionine residue at position 14 being oxidized to methionine sulfoxide. Proof of this structure was accomplished by a peptide mapping procedure that has been described in the literature [Hsiung, H. M., Mayne N. G. and Becker G. W. (1986) Bio/Technology 4, 991-995.]Protein samples (1-2 mg/ml in tris acetate (50 mM, pH 7.5)) were digested with trypsin (TPCK-trypsin, Cooper Biomedical) at 37° C. at an enzyme:substrate weight ratio of 1:25 for 16 hours. The resulting tryptic peptides were separated by reversed-phase HPLC on an Aquapore RP-300 column (4.6 x 250 mm, Brownlee Labs) using a gradient generated from two solvents: A, 0.1% trifluoroacetic acid in water and B, 0.1% trifluoroacetic acid in acetonitrile. The gradient was 0–20% B in 20 minutes, 20–25% B in 20 minutes, and 25–50% in 25 minutes. The flow rate was 1.0 ml/min. A 100 ul aliquot of the tryptic digest was injected onto the column, and elution of the peptides was monitored spectrophotometrically at 214 nm.

Comparison of the peptides generated from the purified derivative of hGH with those arising from unmodified hGH revealed that all of the peptides were the same with one exception. The modified peptide isolated from the trypsin digest of the derivative and shown by automated Edman degradation to have the sequence: Leu-Phe-Asp-Asn-Ala-Met(O)-Leu-Arg. This sequence matches amino acids 9 through 16 of hGH and established that the methionine occurring at position 14 of hGH has been oxidized to methionine sulfoxide. The tryptic peptides containing the other two methionines of hGH occurring at positions 125 and 179 of hGH were unchanged in the derivative when compared with the unmodified hGH.

The biological activity of Met(O)$^{14}$-hGH was assessed in hypophysectomized female Sprague-Dawley rats using the standard tibia assay [Marx. W., Simpson, M. E. and Evans, H. M. (1942pk) *Endocrinology* 30, 1-10; and Evans, H. M., Simpson, M. E., Marx, W. and Kirbrick, E. (1943) *J. Endocrinology* =13-16]. Based on this analysis, the biological activity of Met(O)$^{14}$-hGH is statistically indistinguishable from that of modified hGH.

We claim:
1. Met(O)$^{14}$-human growth hormone.

* * * * *